(12) United States Patent
Chang

(10) Patent No.: US 8,127,766 B2
(45) Date of Patent: Mar. 6, 2012

(54) TRACHEOSTOMY TUBE WITH A SWIVELED CONNECTOR

(76) Inventor: Ti-Li Chang, Taichung Hsien (TW)

( * ) Notice: Subject to any disclaimer, the term of this patent is extended or adjusted under 35 U.S.C. 154(b) by 793 days.

(21) Appl. No.: 12/263,697

(22) Filed: Nov. 3, 2008

(65) Prior Publication Data

US 2010/0108076 A1    May 6, 2010

(51) Int. Cl.
*A61M 16/00* (2006.01)
(52) U.S. Cl. .............................. 128/207.17; 128/207.14
(58) Field of Classification Search ............ 128/207.17, 128/207.15, 207.18, 200.26; 623/9; 604/265
See application file for complete search history.

(56) References Cited

U.S. PATENT DOCUMENTS

| | | | |
|---|---|---|---|
| 4,315,505 A | 2/1982 | Crandall et al. | |
| 5,259,376 A | 11/1993 | Bales | |
| 5,390,669 A | 2/1995 | Stuart et al. | |
| 6,105,577 A * | 8/2000 | Varner | 128/207.17 |
| 6,135,111 A * | 10/2000 | Mongeon | 128/207.15 |
| 7,600,515 B2 * | 10/2009 | Matlock | 128/207.14 |
| 7,681,576 B2 * | 3/2010 | Thomas et al. | 128/207.29 |
| 7,856,983 B2 * | 12/2010 | Blom | 128/207.16 |
| 7,987,851 B2 * | 8/2011 | Blom et al. | 128/207.16 |

FOREIGN PATENT DOCUMENTS

| | | |
|---|---|---|
| DE | 101 40 292 A1 | 3/2003 |
| EP | 1 479 405 A1 | 11/2004 |
| WO | WO 2005/094925 A1 | 10/2005 |
| WO | WO 2007/008418 A1 | 1/2007 |

* cited by examiner

*Primary Examiner* — Jerome W Donnelly
(74) *Attorney, Agent, or Firm* — Alan Kamrath; Kamrath IP Lawfirm, PA

(57) ABSTRACT

A tracheostomy tube has an inserting portion and a connecting portion. The inserting portion has an air way tube, an inflatable cuff and an inflating tube. The connecting portion is connected to the air way tube and has a resilient connector and a connecting sleeve. The resilient connector has a connecting ring connected to the air way tube. The connecting sleeve is mounted around the resilient connector and has a tubular body, a pressing flange formed on the tubular body and at least one slit defined longitudinally in the tubular body and extends through the pressing flange. Movement and vibrations of a patient circuit connected to the tracheostomy tube are not translated into a patient trachea thereby greatly improving patient comfort, safety and quality of life.

11 Claims, 6 Drawing Sheets

TRACHEOSTOMY TUBE WITH A SWIVELED CONNECTOR

BACKGROUND OF THE INVENTION

1. Field of the Invention

The present invention relates to a tracheostomy tube, and more particularly to a tracheostomy tube with a swiveled connector that is easily detachable.

2. Description of Related Art

With reference to FIG. 6, a patient having a neck and a trachea who has difficult breathing due to trachea obstruction, paralysis, genetic, infection or disease caused weakness or drug effects may require a conventional tracheostomy tube (50) inserted into the trachea-through a stoma formed through the trachea to provide air directly to the patient through the tracheostomy tube (50). The conventional tracheostomy tube (50) comprises an inserting portion (52) and a connecting portion (54). The inserting portion (52) is inserted into the trachea of the patient and has an air way tube, an inflatable cuff mounted around the air way tube and an inflating tube connected to the cuff. The connecting portion (54) is attached to the air way tube at a first end and is connected to a patient circuit (30) at a second end.

In use, the inserting portion (52) is inserted into the patient's trachea through the stoma defined in the neck of the patient with the cuff deflated, the cuff is then inflated to expand and abut against an inner surface of the trachea of the patient. The connecting portion (54) is connected to a ventilator through the patient circuit (30). Consequently, air can be forced directly into the trachea of the patient through the tracheostomy tube (50).

However, the conventional tracheostomy tube (50) has the following disadvantages.

1. The connecting portion (54) is securely attached to the inserting portion (52) and connected to the patient circuit (30) and is made of a stiff material. When the patient circuit (30) or ventilator is moved, a shock, vibration or such like is translated directly through the tracheostomy tube (50) and experienced by the patient inside their trachea, causing great discomfort.

2. The connecting portion (54) is securely fitted to the patient circuit (30), so attaching or detaching the patient circuit (30) requires a large force that is translated through a connection between the tracheostomy tube (50) and the neck of the patient causing great discomfort.

3. The aforementioned discomfort caused to the patient is felt as pain and also causes a sick feeling, therefore greatly reducing mobility of the patient may improve their quality of life. The sick feeling may also be a safety concern to caregivers.

To overcome the shortcomings, the present invention tends to provide a tracheostomy tube to mitigate or obviate the aforementioned problems.

SUMMARY OF THE INVENTION

The main objective of the invention is to provide a tracheostomy tube with a swiveled connector that is easily detachable. The tracheostomy tube comprises an inserting portion and a connecting portion. The inserting portion has an air way tube, an inflatable cuff and an inflating tube. The air way tube has an inserting end and a connecting end. The inflatable cuff is mounted around the air way tube near the inserting end. The inflating tube is connected to and communicates with the cuff. The connecting portion is connected to the connecting end of the air way tube of the inserting portion and has a resilient connector and a connecting sleeve. The resilient connector has a connecting end and a connecting ring formed on said connecting end. The connecting end is connected to the connecting end of the air way tube. The connecting sleeve is mounted around the resilient connector and has a tubular body, an annular pressing flange and at least one slit. The tubular body is mounted around the resilient connector and has a pressing end corresponding to the connecting end of the resilient connector. The pressing flange is annular and formed on the pressing end of the tubular body. The at least one slit is defined longitudinally in the tubular body and extends through the pressing flange. Movement and vibrations of a patient circuit connected to the tracheostomy tube with a swiveled connector are not translated into a patient trachea thereby greatly improving patient comfort, safety and quality of life.

Other objects, advantages and novel features of the invention will become more apparent from the following detailed description when taken in conjunction with the accompanying drawings.

DETAILED DESCRIPTION OF PREFERRED EMBODIMENT

Figure 1:
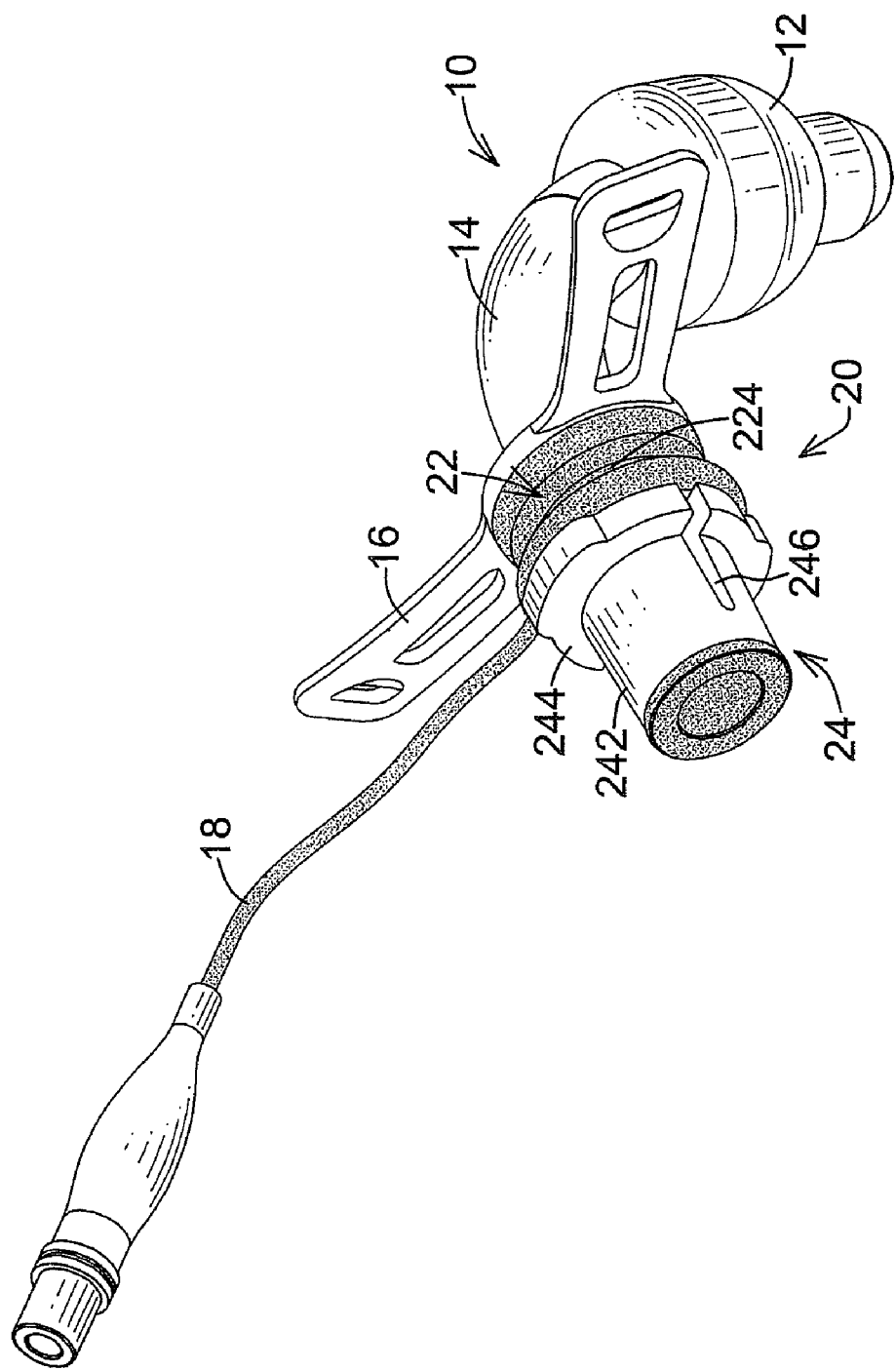
FIG. 1 is a perspective view of a tracheostomy tube in accordance with the present invention.
Figure 2:
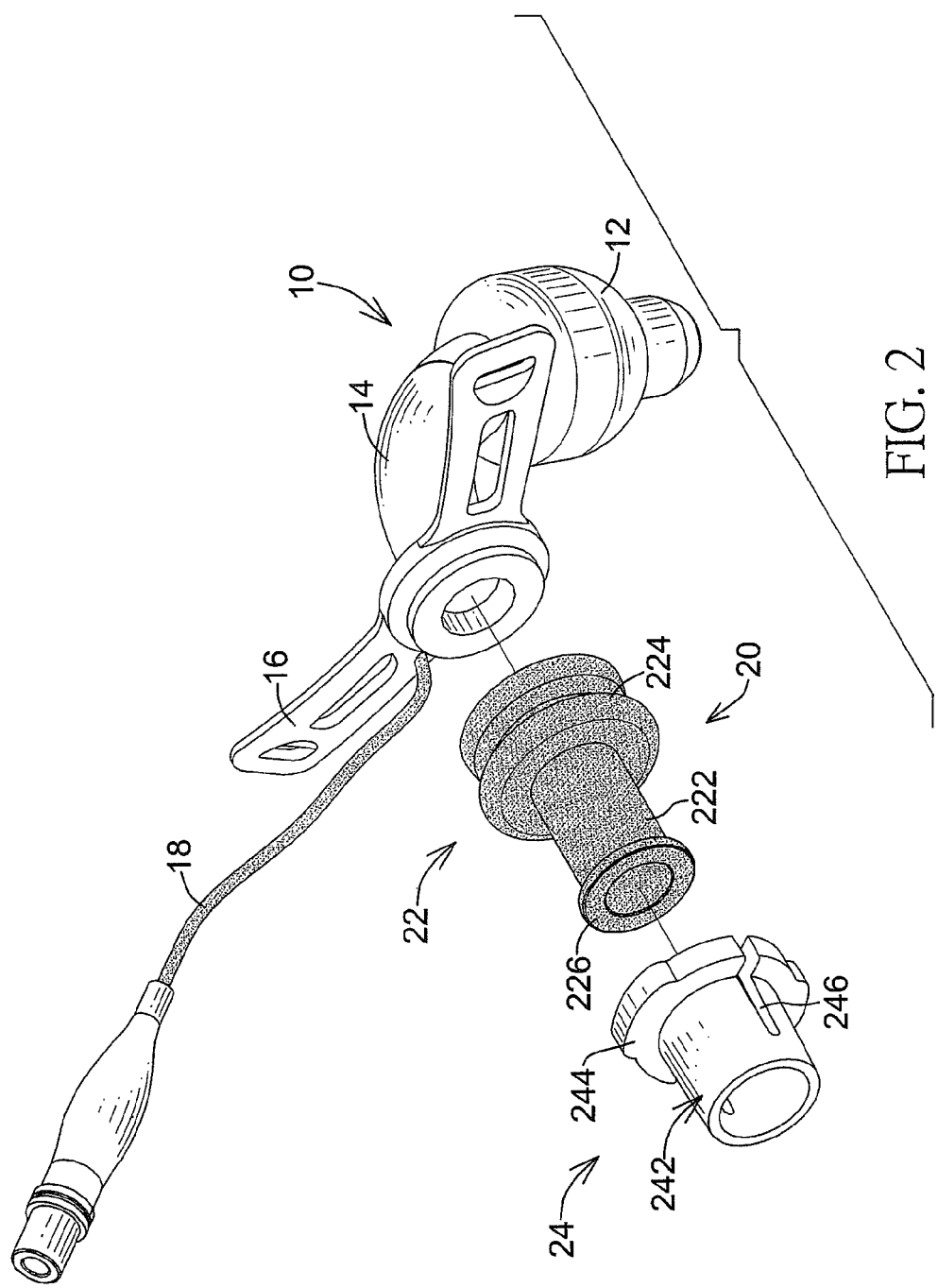
FIG. 2 is an exploded perspective view of the tracheostomy tube in FIG. 1.
Figure 3:
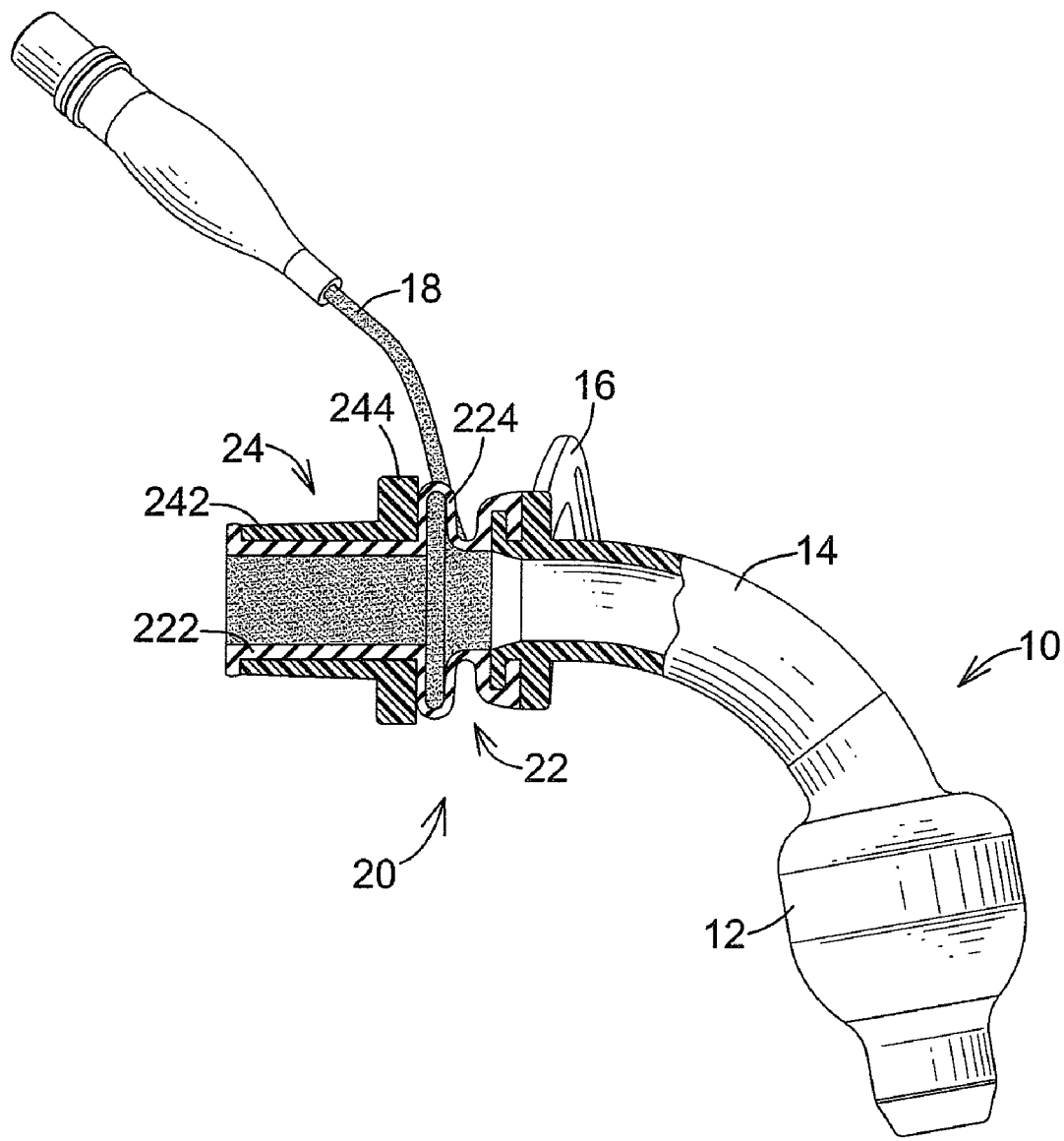
FIG. 3 is a side view in partial section of the tracheostomy tube in FIG. 1.

With reference to FIGS. 1 to 3, a tracheostomy tube in accordance with the present invention comprises an inserting portion (10) and a connecting portion (20). The inserting portion (10) comprises an air way tube (14), an inflatable cuff (12) and an inflating tube (18). The air way tube (14) has an inserting end, a connecting end and two neck plates (16). The inflatable cuff (12) is mounted around the air way tube (14) near the inserting end and is inflated to form a seal in a patient's neck for mechanical breathing or deflated to allow speech and patient breathing spontaneously. The neck plates (16) are formed oppositely on and extend from the connecting end of the air way tube (14) to allow a cord or strap to be mounted around the patient's neck and hold the neck plates (16) in place and hold the inserting portion (10) securely in the neck of the patient. The inflating tube (18) is connected to and communicates with the cuff (12) to allow inflation and deflation.

The connecting portion (20) is connected to the connecting end of the air way tube (14) of the inserting portion (10) and comprises a resilient connector (22) and a connecting sleeve (24). The resilient connector (22) comprises a connecting end, a connecting ring (224), a central tube (222) and a holding flange (226). The connecting end of the resilient connector (22) is connected sealably to the connecting end of the air way tube (14). The connecting ring (224) is resilient and is formed at and protrudes radially from the connecting end of the resilient connector (22). The connecting ring (224) has at least one annular groove defined around the connecting ring (224) to allow asymmetric oscillation of the connecting ring (224). The central tube (222) is formed on and protrudes from the connecting ring (224) and has a distal end. The holding flange (226) is annular and formed on the distal end of the central tube (222), and also serves as an air leak-proof sealing when fitted into the patient circuit. In a preferred embodiment, the central tube (222) and the connecting ring (224) are formed as a single piece.

The connecting sleeve (24) is made of rigid plastic for easy connection with patient circuit and mounted around the resilient connector (22), and is preferably mounted rotatably around the central tube (222) and has a tubular body (242), a pressing flange (244) and at least one slit (246). The tubular body (242) is mounted around the resilient connector, may be mounted rotatably around the central tube (222) and has a pressing end and a linking end. The pressing end corresponds to the connecting end of the resilient connector (22). The linking end is opposite to the pressing end and abuts the holding flange (226) on the central tube (222) to keep the connecting sleeve (24) mounted on the central tube (222) of the connector (22). Therefore, the pressing flange (244) is annular and formed on the pressing end of the tubular body (242). The slit (246) is defined longitudinally in the tubular body (242) and extends through the pressing flange (244) to make the tubular body (242) and pressing flange (244) compressible.

Figure 4:
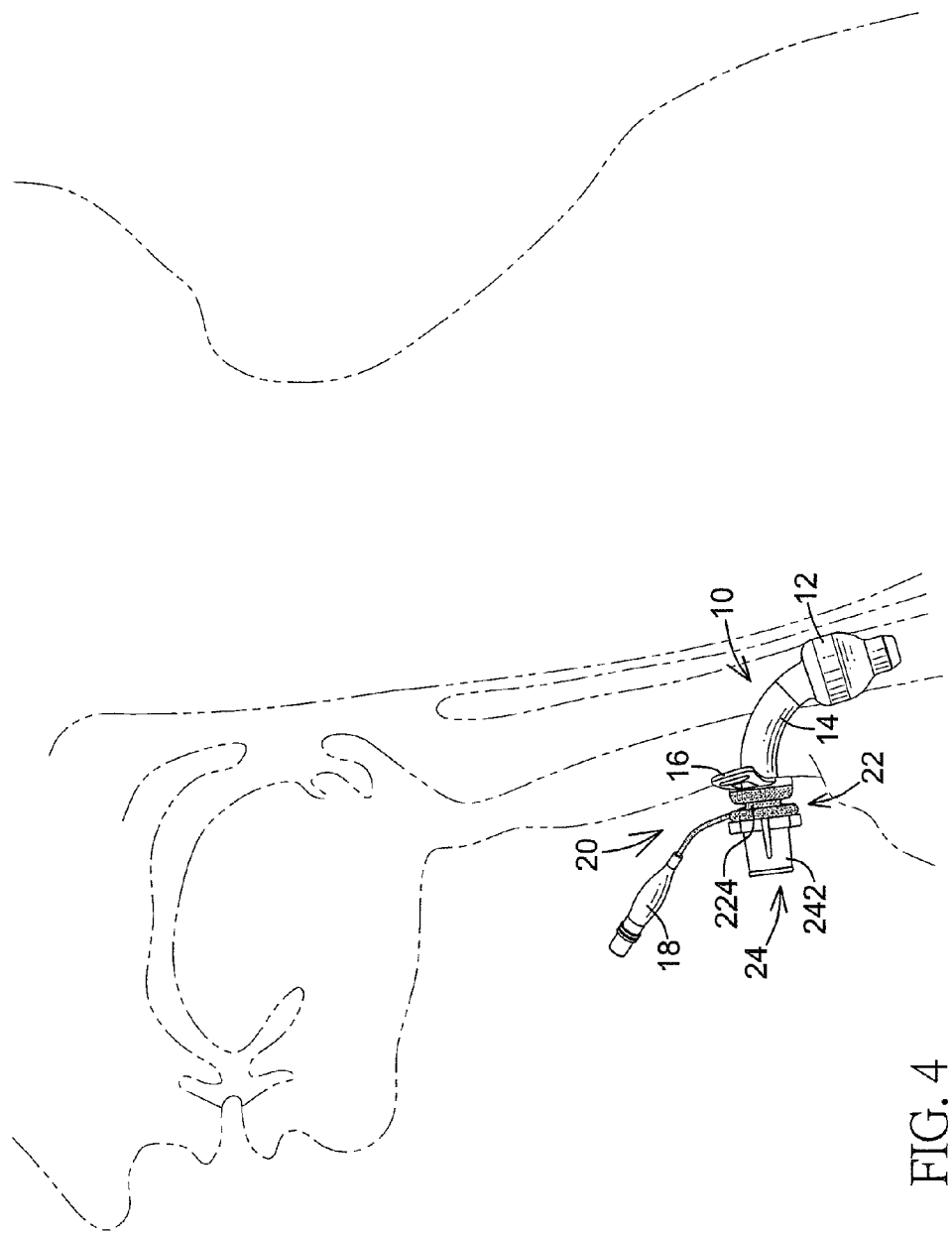
FIG. 4 is an operational side view of the tracheostomy tube in FIG. 1, shown inserted in a trachea of a patient shown in phantom lines.
Figure 5:
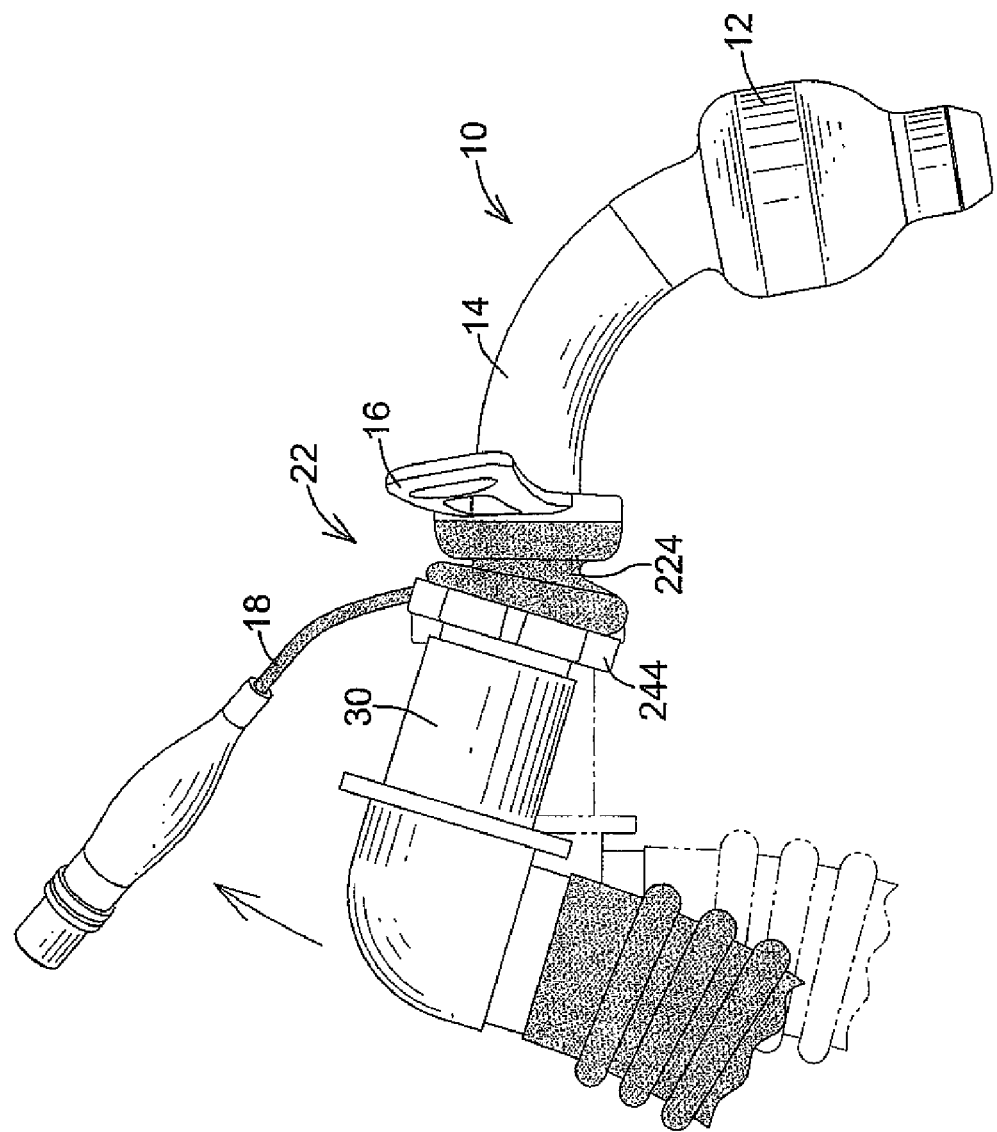
FIG. 5 is an operational side view of the tracheostomy tube in FIG. 1 showing asymmetric oscillation of a connecting ring.
Figure 6:
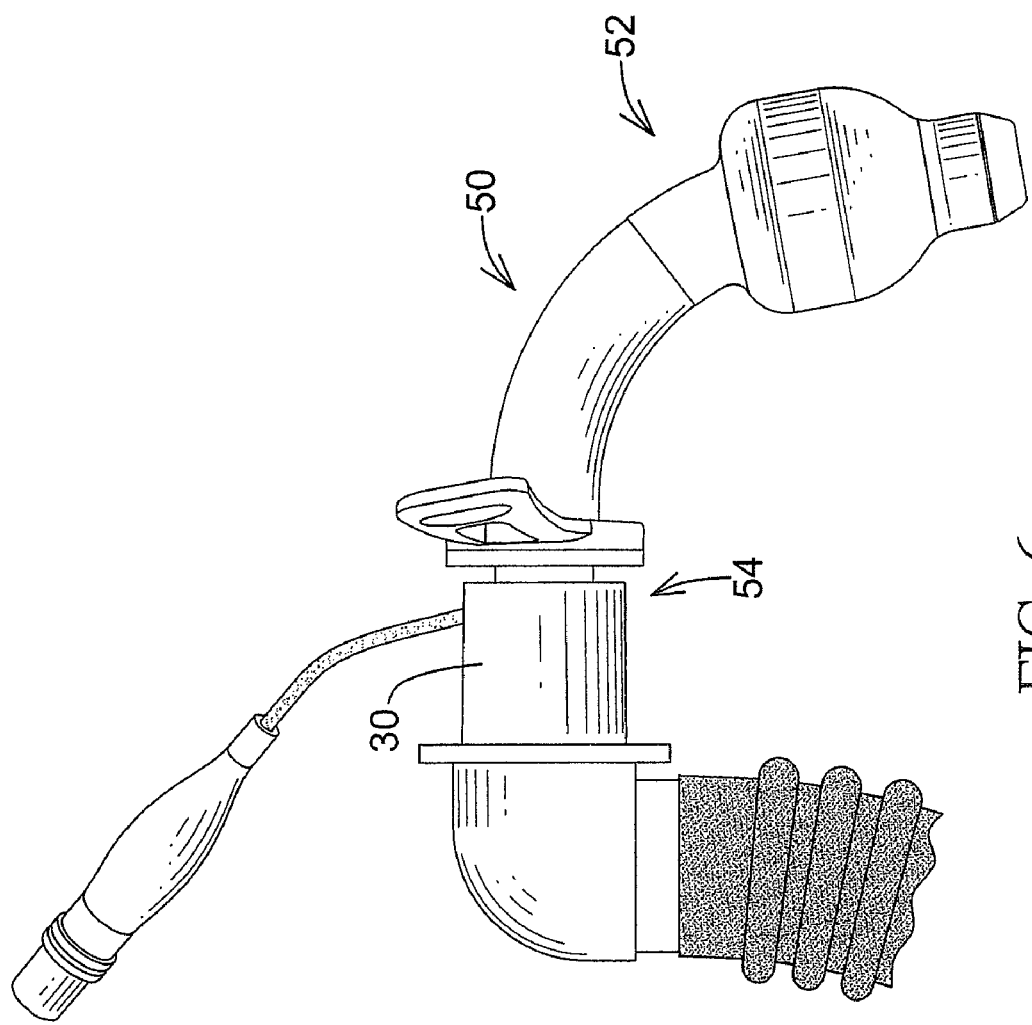
FIG. 6 is a side view of a conventional tracheostomy tube in accordance with the prior art.

With further reference to FIGS. 4 and 5, the inserting portion (10) is inserted into a patient's trachea through a stoma defined in the trachea, the cuff (12) is inflated through the inflating tube (18) and abuts against an inner surface of the patient's trachea. The connecting sleeve (24) of the connecting portion (20) is connected to a ventilator through a patient circuit (30), so that air can be forced directly into the trachea of the patient through the central tube (222) and the connecting ring (224) of the connecting portion (20) and the air way tube (14) of the inserting portion (10).

With such a tracheostomy tube, the connecting ring (224) being resilient and allowed asymmetric oscillatory motion between the inserting portion (10) and the connecting portion (20) and the connector (22) being rotatably mounted around the connecting sleeve (24). The shocks, vibrations or such like movements generated due to movement of the patient, ventilator or patient circuit (30) are prevented from being transmitted to the inserting portion (10). Therefore, the inserting portion (10) is always kept in a stationary condition even when a patient circuit (30) is attached to or detached from the connecting sleeve (24) of the tracheostomy tube, so the patient experiences greater comfort and their quality of life is improved.

Furthermore, the slits (246) in the tubular body (242) of the connecting sleeve (24) allow the connecting sleeve (24) to be compressed by pressing the pressing flange (244) to reduce the diameter of the connecting sleeve (242). Consequently, the patient circuit (30) is easily attached to or detached from the connecting sleeve (24) with the reduced diameter to keep any vibration or shock from occurring at the inserting portion (10) during the attaching or detaching process.

Even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A tracheostomy tube comprising:
   an inserting portion comprising
      an air way tube having an inserting end and a connecting end;
      an inflatable cuff being mounted around the air way tube near the inserting end; and
      an inflating tube connected to and communicating with the cuff; and
   a connecting portion being connected to the connecting end of the air way tube of the inserting portion and comprising
      a resilient connector having
         a connecting end connected to the connecting end of the air way tube; and
         a connecting ring being resilient and formed at and protruding radially from the connecting end of the resilient connector; and
      a connecting sleeve mounted around the resilient connector and having
         a tubular body mounted around the resilient connector and having a pressing end corresponding to the connecting end of the resilient connector;
         a pressing flange being annular and formed on the pressing end of the tubular body; and
         at least one slit being defined longitudinally in the tubular body and extending through the pressing flange.

2. The tracheostomy tube as claimed in claim 1, wherein the resilient connector further comprises a central tube being formed on and protruding from the connecting ring and having a distal end; and
   the tubular body of the connecting sleeve is mounted rotatably around the central tube.

3. The tracheostomy tube as claimed in claim 2, wherein the tubular body of the connecting sleeve has a linking end opposite to the pressing end; and
   the central tube further has a holding flange formed on the distal end of the central tube and abutting the linking end of the tubular body.

4. The tracheostomy tube as claimed in claim 3, wherein the central tube and the connecting ring are formed as a single piece.

5. The tracheostomy tube as claimed in claim 4, wherein the connecting ring has at least one annular groove defined around the connecting ring.

6. The tracheostomy tube as claimed in claim 5, wherein the air way tube has two neck plates formed oppositely on the connecting end of the air way tube.

7. The tracheostomy tube as claimed in claim 2, wherein the central tube and the connecting ring are formed as a single piece.

8. The tracheostomy tube as claimed in claim 7, wherein the connecting ring has at least one annular groove defined around the connecting ring.

9. The tracheostomy tube as claimed in claim 8, wherein the air way tube has two neck plates formed oppositely on the connecting end of the air way tube.

10. The tracheostomy tube as claimed in claim 1, wherein the connecting ring has at least one annular groove defined around the connecting ring.

11. The tracheostomy tube as claimed in claim 1, wherein the air way tube has two neck plates formed oppositely on the connecting end of the air way tube.

* * * * *